United States Patent [19]

Honda et al.

[11] Patent Number: 5,571,512
[45] Date of Patent: Nov. 5, 1996

[54] PHARMACEUTICAL COMPOSITION AGAINST AIDS

[75] Inventors: Mitsuo Honda; Shudo Yamazaki, both of Tokyo; Ryuichi Horie, Kawasaki; Takashi Saito, Ayase; Katsuyoshi Shigeta, Yokohama; Noriyuki Ota, Sagamihara, all of Japan

[73] Assignee: Tosoh Corporation, Shinnanyo, Japan

[21] Appl. No.: 102,218

[22] Filed: Aug. 5, 1993

[30] Foreign Application Priority Data

Aug. 14, 1992 [JP] Japan .................................. 4-237594

[51] Int. Cl.$^6$ .................. A61K 39/395; C07K 16/18; C12N 5/12
[52] U.S. Cl. .................. 424/137.1; 530/387.5; 435/240.27
[58] Field of Search .................. 424/85.8, 137.1; 435/240.27; 530/387.5

[56] References Cited

FOREIGN PATENT DOCUMENTS 0351731  1/1988  European Pat. Off. .

OTHER PUBLICATIONS

Nagai et al. Japan J. Expt. Med. 44(5) pp. 451–464 1974.
Goding Academic Press. p. 59, 1986 2nd ed.
Waldmann Science vol. 252, 1657 1991.
Hird, Genes and Caner Wiley and Sons 1990.
Harris, TibTech vol. 11, 1993 p. 42.
"Composition And Synthesis Of Gangliosides In Mammary Gland And Milk Of The Bovine", *Chemical Abstracts*, 80;23;276, column 1, abstr. #130986, Jun. 1974.
"Isolation And Characterization of A Novel Phytosphingosine–Containing . . . ,", *Journal of Biological Chemistry*, 258;14;8980–85, Jul. 1984.
Hansen et al., "Inhibition of Human Immunodeficiency Virus (HIV) Infection In Vitro by Anticarbohydrate Monoclonal Antibodies: Peripheral Glycosylation of HIV Envelope Glycoprotein gp120 may be a Targer for Virus Neutralization", Journ. of Virology, vol. 64, No. 6, Jun. 1990, pp. 2833–2840.
Adachi et al., "Expression of Le$^y$ Antigen In Human Immunodeficiency Virus–Infected Human T Cell Lines and in Peripheral Lymphocytes of Patients With Acquired Immune Deficiency Syndrome (AIDS) and Aids–Related Complex (ARC)", *Journ. Exp. Med.*, vol. 167, No. 2, Feb. 1988 pp. 323–331, (1988).
Adachi, "Expresion of Le$_y$Antigen in Human Immunodeficiency Virus–Infected Human T Cell Lines and in Peripheral Lymphocytes of Patients with Acquired Immune Deficiency Syndrome (Aids) and Aids–Related Complex (Arc)", Journ. Exp. Med., vol. 167, No. 2, Feb. 1988, pp. 323–331.

*Primary Examiner*—Lila Feisee
*Attorney, Agent, or Firm*—Foley & Lardner

[57] ABSTRACT

A pharmaceutical composition against AIDS, which contains, as an active ingredient, an antibody capable of recognizing glycolipid derived from Echinoidea.

1 Claim, No Drawings

PHARMACEUTICAL COMPOSITION AGAINST AIDS

PHARMACEUTICAL COMPOSITION AGAINST AIDS

The present invention relates to a pharmaceutical composition against AIDS (acquired immune deficiency syndrome), which contains an antibody capable of recognizing glycolipid.

AIDS is a disease which brings about immunodeficiency caused by infection of HIV (human immunodeficiency virus) and which often coincides with pneumocystis carinii or Kaposi's sarcoma. It has been reported that in HIV-infected cells, Lewis Y antigen which is one of carbohydrate antigens, is abnormally expressed (see Adachi et al, J. Exp. Med., 167, p. 323, 1988). Further, it has recently been reported that an antibody capable of recognizing a carbohydrate chain of gp120 which is an HIV coat protein, has inhibited infection of HIV (see Hansen et al, J. Virology, 64, p. 2833, 1990). As is evident from these reports, there is a deep relation between infection of HIV and the carbohydrate chain.

However, it is not known very well what type of carbohydrate chain will be induced in T lymphocytes by the HIV infection or which antibody capable of recognizing carbohydrate chain is effective as a diagnostic agent or a therapeutic agent for AIDS. One of the reasons is that it is difficult to prepare an antibody capable of recognizing a carbohydrate chain having the structure clearly specified.

The present inventors have extracted glycolipid from Echinoidea (sea urchin) and immunized mice with it, whereupon a number of clones have been screened to obtain monoclonal antibodies capable of recognizing such carbohydrate chains. A patent application has already been filed in this connection (Japanese Patent Application No. 131415/1992).

Using such antibodies, the present inventors have now found an expression of the carbohydrate chains on the cell surface by the HIV infection and the effects of such antibodies for inhibiting the HIV infection, and thus have found that the antibodies capable of recognizing Echinoidea-derived glycolipid will be useful as pharmaceuticals for AIDS. The present invention has been accomplished on the basis of this discovery.

Thus, the present invention provides a pharmaceutical composition against AIDS, which contains, as an active ingredient, an antibody capable of recognizing glycolipid derived from Echinoidea.

Now, the present invention will be described in detail with reference to the preferred embodiments.

The pharmaceutical composition in the present invention may, for example, be a diagnostic agent or a therapeutic agent for AIDS. The diagnostic agent for AIDS of the present invention may, for example, be the one for testing the presence or absence of infection of HIV, or the AIDS crisis of a HIV-infected patient or for testing the degree of such infection or crisis. Further, with respect to the test method, the composition of the present invention can be applied to any method employing an antibody, such as an enzymelinked immunosorbent assay (ELISA) or a radioimmunoassay (RIA) by a sandwich method or a competition method as well as a cytofluorometric analysis (FACS).

The therapeutic agent for AIDS of the present invention includes all kinds of therapeutic agents such as a therapeutic agent for preventing further infection from a HIV-infected patient, a therapeutic agent for preventing the AIDS crisis of a HIV-infected patient and a therapeutic agent for delaying the progress of the disease of an AIDS patient. Specifically, a method of administering the antibody by itself or the antibody having a toxin bound thereto as a therapeutic agent, or a method for passing the blood of a patient to a carrier having the antibody preliminarily bound thereto, may, for example, be mentioned.

The antibody to be used in the present invention is the one capable of recognizing Echinoidea-derived glycolipid, particularly glycolipid derived from Echinoidea sperm.

There is no particular restriction as the type of Echinoidea. For example, *Hemicentrotus pulcherrimus* or *Anthocidaris crassispina* may be employed. Likewise, there is no particular restriction as to the method for extracting the glycolipid from Echinoidea. Various methods including extraction with various solvents, may be employed. Extracted glycolipids may, for example, be NeuAcα2→6Glc→Cer, NeuAcα2→8NeuAcα2→6Glc-Cer. These glycolipids may be used for immunization in the form of a mixture as extracted or after being isolated into individual components. Further, such glycolipids may be chemically synthesized.

As a method for preparing the antibody of the present invention, conventional methods and methods employing genetic engineering may, for example, be mentioned. The conventional methods may be classified into a method for a monoclonal antibody and a method for a polyclonal antibody.

In the case of the monoclonal antibody, a hybridoma for producing it, can be prepared by so-called cell fusion. For example, immunization of an animal with an antigen is conducted, for example, by a method wherein glycolipid extracted from Echinoidea is adsorbed on e.g. *Salmonella minnesota* and peritoneally injected to an animal in an amount of from 20 μg to 200 μg per animal dividedly in a few times every three days to four weeks. Here, the animal to be immunized may, for example, be human, a mouse, a rat, a horse, a goat or a rabbit, preferably a mouse, more preferably a BALB/c mouse. The antibody-producing cells of the immunized animal are subjected to cell fusion with myeloma cells. The myeloma cells to be used here, may, for example, be those derived from almost any animal such as a mouse, a rat, human or a rabbit, but they are preferably sp2/0-Ag8 derived from a BALB/c mouse. The cell fusion may be conducted in accordance with the method of Milstain et al with a partial modification. Namely, using from 30 to 60% polyethylene glycol (average molecular weight: 1000–4000), the cell fusion is conducted by a reaction at a temperature of from 30° to 40° C. for from 1 to 3 minutes.

Hybridomas thereby obtained will be subjected to screening by e.g. a solid phase enzyme immunoassay to obtain a hybridoma which produces a monoclonal antibody capable of recognizing glycolipid extracted from Echinoidea. Here, screening is preferably conducted by means of at least 10 plates in a case where each plate has 96 wells. Further, a due care should be taken not to overlook a clone which produces only a small amount of the antibody. Cloning of the hybridoma may be conducted by e.g. a limiting dilution method, a methylcellulose method or a soft agarose method. The hybridoma may be cultured in the same manner as culturing usual animal cells, whereby the antibody to be used in the present invention, will be produced in the culture medium. Otherwise, the hybridoma may be transplanted to e.g. a mouse, so that the monoclonal antibody will be produced in its ascites, and such an antibody may be purified.

The monoclonal antibodies thus obtained, include, for example, SUa-1, SUb-1, SUc-1, SUd-4, SUe-1 and SUf-1, and each of them showed a positive response to Echinoidea-derived glycolipid. Further, they showed a positive response also to the glycolipid fraction derived from human tumor cells. Here, the human tumor cells may specifically be PC-9, COLO201, K562 or LS174T. Further, all of the obtained monoclonal antibodies were of IgM iso type.

Likewise, in a case where a polyclonal antibody is to be used in the present invention, the above-mentioned animal may be immunized with Echinoidea-derived glycolipid in accordance with a conventional method, whereupon the antiserum may be obtained.

On the other hand, in a case where genetic engineering is employed for the preparation of the antibody to be used in the present invention, a mouse may be immunized with Echinoidea-derived glycolipid, whereupon spleen cells are taken out, RNA is extracted and a library of cDNA is prepared, and the desired gene is isolated using the affinity with the antigen as an index. Then, a microorganism or cells having an antibody manifestation vector introduced, may be cultured, followed by purification by a conventional method. For the purification, a usual method such as ammonium sulfate precipitation or salting out, may, for example, be employed.

Thus, the antibody to be used in the present invention may be not only a natural antibody but also an artificial antibody prepared by means of a genetic engineering method or a protein chemistry method. An example of the artificial antibody prepared by a genetic engineering method may be a chimeric antibody wherein the variable region necessary for recognizing the antigen is derived from a mouse and the invariable region unnecessary for recognizing the antigen is derived from human. Preparation of such an antibody can be conducted by a method per se well known in the art. Further, as an example of the artificial antibody prepared by a protein chemistry method, a fragmented antibody such as Fab which can be prepared by digesting an antibody molecule by papain, may be mentioned.

Now, the present invention will be described in further detail with reference to Examples. However, it should be understood that the present invention is by no means restricted to such specific Examples.

EXAMPLE 1

(1) Preparation of an Antigen Used for Immunization and Screening

To 0.5 g of freeze-dried sperm of *Hemicentrotus pulcherrimus*, four times by volume of methanol was added, and the mixture was homogenized. Then, ten times by volume of chloroform/methanol (1/2, v/v) was added thereto, followed by filtration under reduced pressure. This operation was repeated three times. Further, extraction at the boiling point was conducted once with five times by volume of chloroform/methanol (1/2, v/v) and once with five times by volume of chloroform/methanol (2/1, v/v). Finally, extraction with ten times by volume of chloroform/methanol/water (4/8/3, v/v/v) was repeated three times. The respective extracts were put together, and the solvents were distilled off. The residue was washed three times with cold acetone and then subjected to Folch partition. Then, the lower layer was subjected to DEAE-Sephadex A-25 column (2.2 cm×53 cm) to obtain eluted glycolipids fraction. The upper layer was subjected to dialysis and freeze drying and then to an anion exchange column in the same manner as for the above lower layer, to recover glycolipids fraction. The two were put together to obtain extracted glycolipid (9.4 mg).

(2) Method for Sensitizing an Animal

210 µg of the glycolipid extracted in Step (1) was adsorbed on 800 µg of *Salmonella minnesota* strain and peritoneally injected for immunization to a Balb/c mouse in accordance with a schedule of 15 µg on the first day, 30 µg on the fourth day, 45 µg on the 7th day, 60 µg on the 12th day and 60 µg on the 24th day. Three days after the final injection for immunization, the spleen of the mouse was harvested and used for the following cell fusion.

(3) Cell Fusion and Cloning

The mouse spleen cells and mouse myeloma cells SP2/0 were mixed at a ratio of 10:1 and reacted for 2 minutes using 50% polyethylene glycol (average molecular weight: 4000) to conduct cell fusion. The obtained cells were planted on a 96 well microtiter plate and cultured for from 7 to 14 days in a HAT culture medium. The supernatant of the propagated cell culture was subjected to screening by a solid phase enzyme immunoassay, and cloning was conducted with respect to cells in a well showing a positive response.

Namely, the cells in a well in which the supernatant of the culture showed a positive response as a result of the solid phase enzyme immunoassay, were diluted with an E-RDF culture medium to a concentration of 1 cell/0.2 ml, and 0.2 ml was transplanted to each well of a 96 well microtiter plate. In ten days after the initiation of culturing, a colony identifiable by a naked eye was formed, with respect to the colony thus obtained, screening and cloning were conducted in the same manner.

(4) Method for Screening

With respect to a hybridoma obtained by the above method, screening of a clone which produces the desired monoclonal antibody, was conducted by the following solid phase enzyme immunoassay against the glycolipid extracted from the sperm of *Hemicentrotus pulcherrimus*.

(a) Method for Coating the Antigen (The Glycolipid) onto a 96 Well Microtiter Plate.

The glycolipid of the sperm of *Hemicentrotus pulcherrimus* obtained by the above described method was adjusted to 100 µg/ml with ethanol containing 5 µg/ml of phosphatidyl choline and 2.5 µg/ml of cholesterol. The adjusted ethanol solution of the glycolipid was injected to each well in an amount of 20 µl each and dried on a hot plate of about 37° C. Using PBS (containing 5% of BSA), blocking was conducted at 4° C. overnight to prevent unspecified reactions, and then the microtiter plate was used for screening.

(b) Solid Phase Enzyme Immunoassay

To the 96 well microtiter plate prepared by the method of Step (a), a test sample was added and reacted at room temperature for one hour, followed by washing. Then, a peroxidase-labelled anti-mouse immunoglobulin (IgG+ IgM) goat antibody was added thereto and further reacted at room temperature for one hour. After removing the unreacted labelled-antibody by washing, an ABTS substrate solution was added thereto and reacted at room temperature for 10 minutes. Then, the reaction was stopped by adding 0.5 M oxalic acid, and the absorbance at 415 nm was measured.

As described in the foregoing, six types of single clone strains of SUa-1, SUb-1, SUc-1, SUd-4, SUe-1 and SUf-1 showing a positive response to the desired antigen were obtained.

(5) Specificity of Monoclonal Antibodies (a) Immunoglobulin Class

The immunoglobulin classes of the monoclonal antibodies SUa-1, SUb-1, SUc-1, SUd-4, SUe-1 and SUf-1 produced by the clone strains thus screened, were all determined to be IgM by the solid phase enzyme immunoassay.

(b) Reactivity with Glycolipid

The reactivity of the monoclonal antibodies SUa-1, SUb-1, SUc-1, SUd-4, SUe-1 and SUf-1 thus obtained, with various glycolipids, was studied. The glycolipid derived from sperm of *Hemicentrotus pulcherrimus* and glycolipids derived from various cancer cells as identified in Table 1, were, respectively, fixed on a 96 well microtiter plate, and their reactivities with the monoclonal antibodies SUa-1, SUb-1, SUc-1, SUd-4, SUe-1 and SUf-1 were studied, respectively, by the same solid phase enzyme immunoassay as used for screening. The results are shown in Table 1.

TABLE 1

|   | SUa-1 | SUb-1 | SUc-1 | SUd-4 | SUe-1 | SUf-1 |
|---|---|---|---|---|---|---|
| A | + | + | + | + | + | + |
| B | + | + | + | + | + | + |
| C | − | − | − | − | − | − |
| D | + | + | + | + | + | + |
| E | + | + | + | + | + | + |
| F | + | + | + | + | + | + |
| G | − | − | − | − | − | − |
| H | + | + | + | + | + | + |

A: Glycolipid extracted from sperm of *Hemicentrotus pulcherrimus*
B: Glycolipid containing one sialic acid extracted from PC-9 cells
C: Glycolipid containing two sialic acids extracted from PC-9 cells
D: Glycolipid containing one sialic acid extracted from LS-174T cells
E: Glycolipid containing two sialic acids extracted from LS-174T cells
F: Glycolipid containing one sialic acid extracted from K562 cells
G: Glycolipid containing two sialic acids extracted from K562 cells
H: Glycolipid containing one sialic acid extracted from COLO201 cells (6) Recognition of HIV-Infected Cells by Monoclonal Antibodies Capable of Recognizing Glycolipid The reactivities of various monoclonal antibodies capable of recognizing glycolipid, to the HIV-infected cells, were examined. As the antibodies, a control mouse antibody and monoclonal antibody SUb-1 were employed. As HIV, Bru of type 1 (see Barre-Sinoussi et al, Science, 220, p.868, 1983) and Rod of type 2 (see Clavel et al, Science, 233, p.343, 1986) were employed. As the infected cells, T-cell line H9, lymphoma cell U937, lymphocyte PHA blast and macrophage PHA blast were employed. The staining test employing a cytofluorometric analysis (FACS) was conducted in accordance with the method described by Honda et al, J. Immunology, 145, p.4131, 1990.

Results are shown in Tables 2 and 3. The Tables 2 and 3 show the proportions (%) in which various HIV-infected cells were stained by various antibodies. As is apparent from the Tables, when Rod was infected to macrophage PHA blast, the proportion of the cell stain with SUb-1 increased, and when Rod was infected to lymphoma cells U937, the proportion of cell stain with SUb-1 decreased. Thus, it is understood that this method presents a method for detecting AIDS-infected cells by an antibody recognizing Echinoidea-derived glycolipid and that such an antibody is useful as a diagnostic agent for AIDS.

EXAMPLE 2

Inhibition of HIV Infection by Various Monoclonal Antibodies Capable of Recognizing Glycolipid The effects of inhibiting infection of HIV to cells by various monoclonal antibodies capable of recognizing glycolipid, were examined. The same antibodies as used in Example 1, were employed. As HIV, NDK of a type which requires no CD4 antigen for its infection (see Chermann et al, Human Retroviruses (eds. Stehelin, D.) 14, 1988), Bru of type 1 and Rod of type 2 were employed. As the infected cells, U937 lymphoma cells were employed. The degree of infection was measured by a solid phase enzyme immunoassay (ELISA) using an anti p24 antibody to a p24 antigen as a core protein of HIV. The measurement was conducted on the day on which HIV was infected to various cells, on the third day and the seventh day by measuring the amount of p24 (pg/ml) in the infected cells.

The results are shown in Tables 4 and 5. As is apparent from these Tables, infection of HIV to cells is inhibited by the antibodies capable of recognizing Echinoidea-derived glycolipid. For example, infection of NDK was completely inhibited by SUb-1, and an inhibitory action was observed also against infection of Rod.

From the foregoing results, it is evident that this method presents a method for analyzing the effects for inhibiting infection of HIV to cells by antibodies capable of recognizing Echinoidea-derived glycolipid, and that such antibodies are useful as therapeutic agents for AIDS.

TABLE 2

Unit (%)

| | Cell | | | | |
|---|---|---|---|---|---|
| | H9 | | U937 | | |
| | Virus | | | | |
| Antibody | (−) | Bru | (−) | Bru | Rod |
| Control | 0.7 | 1.0 | 0.7 | 0.7 | 0.9 |
| SUb-1 | 0.8 | 0.6 | 11.0 | 13.2 | 2.7 |

TABLE 3

Unit (%)

| | Cell | | | | |
|---|---|---|---|---|---|
| | PHA blast (lymphocyte) | | | PHA blast (macrophage) | |
| | Virus | | | | |
| Antibody | (−) | Bru | Rod | (−) | Bru | Rod |
| Control | 1.0 | 1.0 | 1.0 | 0.9 | 0.8 | 1.0 |
| SUb-1 | 22.9 | 27.1 | 22.7 | 8.9 | 13.4 | 33.8 |

TABLE 4

Unit (pg/ml)

| | Cell | | | | | |
|---|---|---|---|---|---|---|
| | NDK | | | Bru | | |
| | Number of days | | | | | |
| Antibody | 0 | 3 | 7 | 0 | 3 | 7 |
| Control | ND | ND | 140.0 | ND | 127.3 | 531.0 |
| SUb-1 | ND | ND | ND | 113.0 | 167.2 | 449.3 |

TABLE 5

| | Unit (pg/ml) | | |
|---|---|---|---|
| | | Rod Number of days | |
| Antibody | 0 | 3 | 7 |
| Control | ND | ND | 606.5 |
| SUb-1 | ND | ND | 356.3 |

The application of the antibodies capable of recognizing Echinoidea-derived glycolipid to diagnostic and therapeutic agents for AIDS according to the present invention, is expected to contribute substantially to the diagnosis and therapy of AIDS which is expected to increase in the future.

Further, by researches using such antibodies, it is expected that basic researches for HIV infection and AIDS crisis will progress, and detailed mechanisms will be clearly understood.

We claim:

1. An immunoreactive composition comprising a monoclonal antibody capable of recognizing glycolipid extracted from sperm of *Hemicentrotus pulcherrimus*, wherein said antibody also binds to glycolipid extracted from LS-174T cells, K562 cells and COLO201 cells, and wherein said antibody binds a least one glycolipid selected from the group consisting of NeuAcα2→6Glc→Cer and NeuAcα2→8NeuAcα2→6Glc-Cer.

* * * * *